(12) United States Patent
Medow et al.

(10) Patent No.: US 12,728,223 B2
(45) Date of Patent: Sep. 8, 2026

(54) ORAL BITE BLOCK FOR ENDOTRACHEAL TUBE

(71) Applicant: Wisconsin Alumni Research Foundation, Madison, WI (US)

(72) Inventors: Joshua Medow, Verona, WI (US); Matthew Roggensack, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 637 days.

(21) Appl. No.: 18/139,155

(22) Filed: Apr. 25, 2023

(65) Prior Publication Data

US 2024/0358952 A1 Oct. 31, 2024

(51) Int. Cl.
*A61M 16/04* (2006.01)

(52) U.S. Cl.
CPC .... *A61M 16/0493* (2014.02); *A61M 16/0497* (2013.01); *A61M 2210/0637* (2013.01)

(58) Field of Classification Search
CPC .......... A61M 16/0493; A61M 16/0488; A61M 16/0497; A61M 2210/0637; A61M 16/049; A61M 2209/088; A61C 7/08; A61F 5/566; A63B 71/085; A63B 2071/086
See application file for complete search history.

(56) References Cited

U.S. PATENT DOCUMENTS

| | | | | |
|---|---|---|---|---|
| 5,235,991 A * | 8/1993 | Minneman | A63B 71/085 | 433/140 |
| 5,386,821 A * | 2/1995 | Poterack | A61M 16/0493 | 128/207.14 |
| 5,537,994 A * | 7/1996 | Thornton | A61F 5/566 | 128/207.18 |
| 5,562,106 A * | 10/1996 | Heeke | A61F 5/566 | 128/848 |
| 7,004,172 B1 * | 2/2006 | Zacco | A61F 5/566 | 128/848 |
| 8,567,408 B2 * | 10/2013 | Roettger | A61C 5/90 | 128/861 |
| 2002/0095119 A1 * | 7/2002 | Bertoch | A61M 25/02 | 604/179 |
| 2007/0197876 A1 * | 8/2007 | Lane | A61M 16/0493 | 600/195 |
| 2013/0146068 A1 * | 6/2013 | Van Wagenen | A61M 16/0493 | 128/862 |
| 2015/0223968 A1 * | 8/2015 | Hervy | A61F 5/56 | 128/848 |

* cited by examiner

*Primary Examiner* — Brandy S Lee
*Assistant Examiner* — Sara K Toich
(74) *Attorney, Agent, or Firm* — Boyle Fredrickson, S.C.

(57) ABSTRACT

A bite block provides a pair of bilateral jaw spacers positioned between the patient's posterior teeth to separate an interincisal distance between the jaw. A connecting bridge behind the patient's incisors joins the bilateral spacers at opposite sides of the jaw. The bilateral jaw spacers are positioned between the patient's upper and lower posterior teeth to transfer the forces against the bite block when the patient bites down to the stronger and wider posterior teeth that can withstand larger stresses. The posterior teeth have large, flat surfaces which can stably receive the bilateral jaw spacers without unwanted displacement.

18 Claims, 2 Drawing Sheets

16 10 90 94 92 24 θ 14 26 12 20 23 22 14

ORAL BITE BLOCK FOR ENDOTRACHEAL TUBE

STATEMENT REGARDING FEDERALLY SPONSORED RESEARCH OR DEVELOPMENT

--

CROSS REFERENCE TO RELATED APPLICATION

--

BACKGROUND OF THE INVENTION

The present invention relates to medical devices and, in particular, to a bite block or bite guard preventing biting compression of the endotracheal tube occluding airflow during endotracheal intubation.

An endotracheal intubation may be performed on patients who are critically injured where their airway becomes blocked or damaged, or the patient becomes unable to breathe spontaneously. Generally, an endotracheal tube is a tube constructed of polyvinyl chloride, rubber, or silicone that is placed between the vocal cords through the windpipe (trachea) and out the mouth during tracheal intubation. It serves to provide oxygen and gases to the lungs and protects the lungs from contamination from gastric contents or blood. The endotracheal tube is flexible thus allowing the tube to bend through the mouth into the windpipe and between the vocal cords.

An endotracheal tube is often placed when a patient is unconscious, for example, when a patient is under anesthesia or in a coma. Because of the discomfort caused by the intubation procedure, if the endotracheal tube is placed while the patient is conscious, medication may be used to ease the pain and anxiety while the endotracheal tube is being placed.

When it is confirmed that the endotracheal tube is in the proper position within a patient's windpipe, a balloon cuff may be inflated on the internal end of the endotracheal tube to keep the endotracheal tube from moving out of the place, and the external end of the endotracheal tube may be taped or strapped to the outside of the patient's face to secure tube placement.

A hard and rigid tubular bite block may be used to prevent the patient from biting down on the endotracheal tube, compressing the tube and obstructing airflow. The external end of the endotracheal tube is inserted through the rigid bite block tube and the rigid bite block tube is held between the patient's lips and front teeth (incisors). The rigid bite block tube surrounds the endotracheal tube and is fastened to a strap extending around the patient's head to secure the bite block tube and endotracheal tube in place. The rigid bite block tube ensures that the endotracheal tube is held securely in place and that the patient does not compress the endotracheal tube when biting down, thus, undesirably occluding the endotracheal tube and preventing proper airflow to the lungs.

The patient's incisors at the front of the mouth can place a large amount of force on the rigid bite block tube as the patient bites down (e.g., when clenching or grinding their teeth) and in return, the rigid bite block tube places a large amount of force and stress on the patient's teeth. This high amount of force and stress on the teeth from the patient's biting translates to loosening of the patient's incisors at the front of the mouth. When the patient is unconscious, they are unaware of the large amount of force stress they are placing on the rigid bite block tube and their teeth. Additionally, injury or trauma to the patient's lips, tongue, floor of the mouth, or inner lining of lips or cheeks (buccal mucosa) can occur through rubbing or movement of the hard bite block within the patient's mouth during intubation.

Therefore, there is a desire to eliminate these unwanted side effects and complications associated with endotracheal intubation.

SUMMARY OF THE INVENTION

The present invention provides a bite block that improves upon existing bite block tubes by relocating the bite block from the front of the jaw to the rear of the jaw, where instead of a single hard and rigid tube placed between the patient's incisor teeth, a pair of bilateral jaw spacers are wedged between the patient's posterior teeth (i.e., molars and/or premolars) to separate the jaw at the rear of the mouth. The patient's posterior teeth can better withstand the high forces placed on and by the bilateral jaw spacers than the incisor teeth. A connecting bridge behind the patient's incisors (i.e., maxillary incisor teeth and/or mandibular incisor teeth) joins the bilateral jaw spacers (at opposite rear left and right sides of the patient's jaw) to provide a bilateral unitary device with equal lateral force distribution.

In use, the bilateral jaw spacers are wedged between the patient's left and right, upper and lower posterior teeth to transfer the forces against the bite block when the patient bites down to the stronger and wider posterior teeth that can withstand larger forces and stresses. Further, by anatomical design, the posterior teeth have large, flat contact surfaces which can more stably receive the bilateral jaw spacers and associated forces without unwanted movement compared to the incisors.

One embodiment of the present invention provides a bite block device for inhibiting a biting force on an endotracheal tube extending through a human patient's mouth, the bite block device comprises a first molar spacer configured to contact left maxillary posterior teeth on a top surface and left mandibular posterior teeth on a bottom surface; a second molar spacer configured to contact right maxillary posterior teeth on a top surface and right mandibular posterior teeth on a bottom surface; and a curved bridge connecting the top end of the first molar spacer at a first end to the top end of the second molar spacer at a second end and extending forwardly to a curved center portion configured to extend along a lingual surface of maxillary incisors.

It is thus a feature of one embodiment of the present invention to provide bilateral support to the mouth to relieve stress and force on the temporomandibular joint (TMJ) caused by one sided grinding or clenching of the teeth and associated with TMJ joint disorders and pain in the joint.

The first molar spacer and second molar spacer may be fixedly attached to the curved bridge.

It is thus a feature of one embodiment of the present invention to allow for easier insertion of two spaced, bilateral spacers using a singular mouthpiece that resembles a mouthguard or retainer familiar to patients.

The first end and second end of the curved bridge may extend upwardly from the top end of the first molar spacer and the top end of the second molar spacer, respectively.

It is thus a feature of one embodiment of the present invention to inhibit the patient from removing the bite block from their mouth with their tongue where natural upward force of the tongue against the bridge does not dislodge the bite block bridge wedged behind the patient's incisors.

The curved center portion may dip downwardly and further extend at an upward angle.

It is thus a feature of one embodiment of the present invention to minimize bite block contact with the patient's incisors and thus eliminate forces from being applied to and damaging the patient's incisors.

The curved bridge may not contact the patient's buccal mucosa or lips.

It is thus a feature of one embodiment of the present invention to prevent mouth sores that occur when the patient's buccal mucosa and lips contact and rub or scrape against the bite block.

A distance between the first end and the second end of the curved bridge may be approximately equal to a width of an upper jaw of the patient.

It is thus a feature of one embodiment of the present invention to accommodate a width of the patient's jaw which may vary between differently sized patients.

The distance between the first end and the second end of the curved bridge may be at least 25 mm. The distance between the first end and the second end of the curved bridge may be at least 50 mm.

It is thus a feature of one embodiment of the present invention to eliminate bite blocks from contacting the incisors where weaker incisor teeth cannot withstand as much force as the posterior teeth.

A tab may extend forwardly from the curved bridge. A medical tubing may be attached to the tab.

It is thus a feature of one embodiment of the present invention to allow the endotracheal tube to be attached and fastened to the bite block outside of the patient's mouth to secure the position of the external end of the endotracheal tube without contacting the patient's lips and to avoid accidental extubation.

The first and second molar spacers may be wedge shaped blocks tapering from a broad front end to a narrow rear end.

It is thus a feature of one embodiment of the present invention to allow the molar spacers to be more easily forced into the narrow space between the patient's posterior teeth when the patient is unconscious and the patient's jaw may be clenched.

A height of the broad front end of the first and second molar spacers may be at least 10 mm.

It is thus a feature of one embodiment of the present invention to create a wide enough jaw opening angle by inserting wedges near the jaw angle between the posterior teeth thus optimizing the wedge angles.

A length of the first and second molar spacers extending across the first and second molars of the patient may be at least 40 mm.

It is thus a feature of one embodiment of the present invention to distribute the biting force onto multiple posterior teeth which minimizes the damage to any individual tooth.

An angle of mouth opening with respect to a patient's temporomandibular joint may be at least 20 degrees. The first and second molar spacer may be configured to create an interincisal distance between an incisal edge of maxillary central incisors of an upper jaw of the patient and an incisal edge of mandibular central incisors of a lower jaw of the patient of at least 11 mm.

It is thus a feature of one embodiment of the present invention to keep the mouth opening wide enough to prevent any biting force to be exerted onto the endotracheal tube where the largest endotracheal tube has an outer diameter of about 11 mm. It is also a feature of one embodiment of the present invention to minimize discomfort and joint injury to the patient associate with overly wide mouth opening angles.

The first and second molar spacer may not contact buccal surfaces of the posterior teeth of the patient.

It is thus a feature of one embodiment of the present invention to permit lateral access to the patient's posterior teeth for toothbrush cleaning thus removing the buccal flanges that may exist with other mouth appliances such as dentures.

A second curved bridge may connect the bottom end of the first molar spacer and the bottom end of the second molar spacer and may extend forwardly to a curved front end configured to extend along the lingual surface of the mandibular incisors.

It is thus a feature of one embodiment of the present invention to provide additional structural support between the molar spacers to stabilize the widely spaced apart molar spacers.

One embodiment of the present invention provides a method of inhibiting a biting force on an endotracheal tube extending through a human patient's mouth, the method including the steps of: providing a bite block having a first molar spacer configured to contact left maxillary posterior teeth on a top surface and left mandibular posterior teeth on a bottom surface; a second molar spacer configured to contact right maxillary posterior teeth on a top surface and right mandibular posterior teeth on a bottom surface; and a curved bridge connecting the top end of the first molar spacer at a first end to the top end of the second molar spacer at a second end and extending forwardly to a curved center portion configured to extend along a lingual surface of maxillary incisors. The method comprises positioning the first molar spacer between the left maxillary posterior teeth and the left mandibular posterior teeth. The method comprises positioning the second molar spacer between the right maxillary posterior teeth and right mandibular posterior teeth. The method comprises positioning the curved bridge along the lingual surface of the maxillary incisors.

The method may include distributing a biting force of the patient onto the first molar spacer and the second molar spacer.

The method may include attaching an endotracheal tube to the bite block.

These particular objects and advantages may apply to only some embodiments falling within the claims and thus do not define the scope of the invention.

BRIEF DESCRIPTION OF THE DRAWINGS

FIG. 2 is a partial enlarged right side elevation view of the bite block of FIG. 1 showing a jaw spacer of the bite block engaging the upper and lower posterior teeth of a right side of a patient's jaw, where an identical, mirrored jaw spacer is positioned on an opposite left side of the patient's jaw;

DETAILED DESCRIPTION OF THE PREFERRED EMBODIMENT

Figure 1:
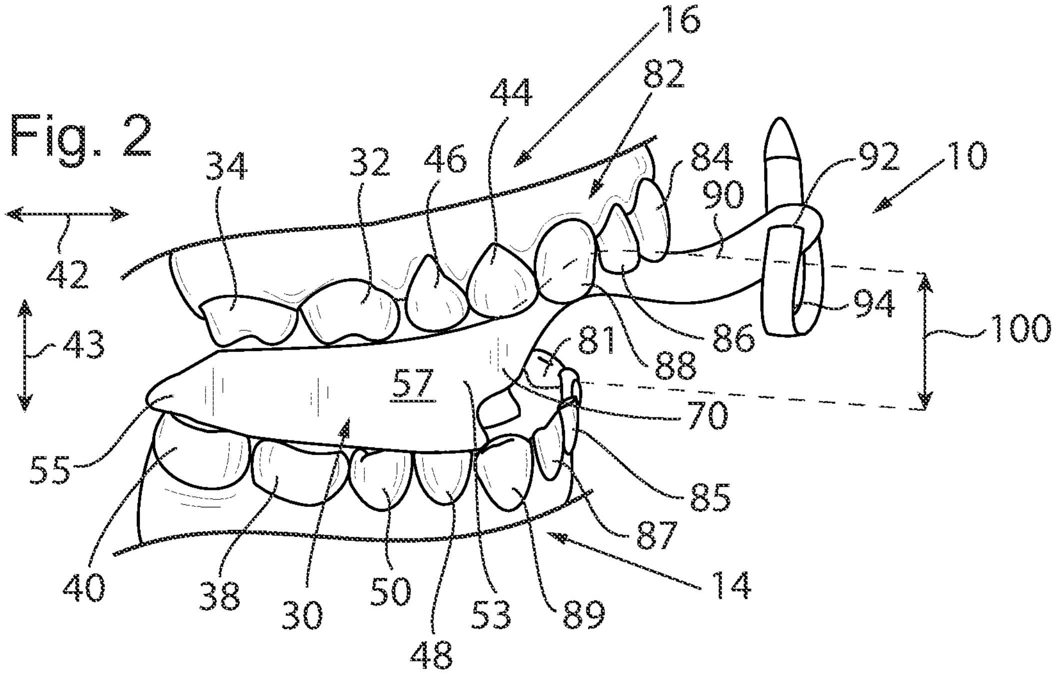
FIG. 1 is a side perspective view of a bite block of the present invention being worn by an adult human patient with an endotracheal tube inserted through the patient's mouth and drawn down into the patient's trachea, where the bite block is positioned between the patient's upper and lower posterior teeth and behind the upper incisors to sustain the patient's jaw open at an angle to prevent compression of the endotracheal tube.

Referring to FIG. 1, a bite block 10 according to the present invention may be inserted, for example, within a mouth 12 of a human patient 14 to support the bite block 10 within the mouth 12 between the upper jaw 16 and lower jaw 18 and behind the upper incisors (and optionally, lower incisors) of the patient 14. The bite block 10 is inserted into the mouth 12 of the patient 14 during endotracheal intubation of the patient 14 whereby a healthcare provider will insert an endotracheal tube 20 through a patient's mouth 12 and into the trachea 22 of the patient 14 between the vocal cords. As understood in the art, the endotracheal tube 20 keeps the trachea 22 open so that air can get into the lungs of the patient 14 or in some instances, to administer drugs.

The endotracheal tube 20 is a flexible tube commonly made of polyvinyl chloride, rubber, silicone, silicone rubber, latex rubber, and the like, that can bend to be inserted through the air pathways of the patient 14. An internal end 23 of the endotracheal tube 20 may include an inflatable balloon cuff 26 to help secure the endotracheal tube 20 in place, to prevent leakage of respiratory gases, and to protect a tracheobronchial tree from receiving undesirable material such as stomach acid as understood in the art. An external end 24 of the endotracheal tube 20 extends out of the mouth 12 of the patient 14 (e.g., extending externally about 20 to 50 mm) where a T-piece, anesthesia breathing circuit, bag valve mask device, or a mechanical ventilator may be attached as understood in the art.

The endotracheal tube 20 may range in length from 200 to 350 mm and range from 2.0 to 10.5 mm in internal diameter and 2.5 to 11 mm in outer diameter. The size of the endotracheal tube 20 is chosen based on the patient's body size. In a similar manner, the bite block 10 may come in different sizes and the size of the bite block 10 may be chosen based on the patient's jaw size. It is contemplated that a set of standardized bite block sizes (e.g., small child, average child, average adult, large adult) would fit a majority of patients and may be sold in a kit, as further described below.

The bite block 10 may be used in conjunction with the endotracheal tube 20 at the external end 24 in order to prevent the patient 14 from compressing the endotracheal tube 20 with their teeth or jaw, to prevent mucosal pressure ulcers on the lips, mouth, gums and tongue caused by tracheal intubation, and to secure the external end 24 of the endotracheal tube 20 to the patient's mouth. The bite block 10 also assists with preventing accidental extubation or adverse endotracheal tube 20 movement (i.e., vertical or horizontal displacement) by movement of the tongue or jaw of the patient 14.

Figures 3, 4:
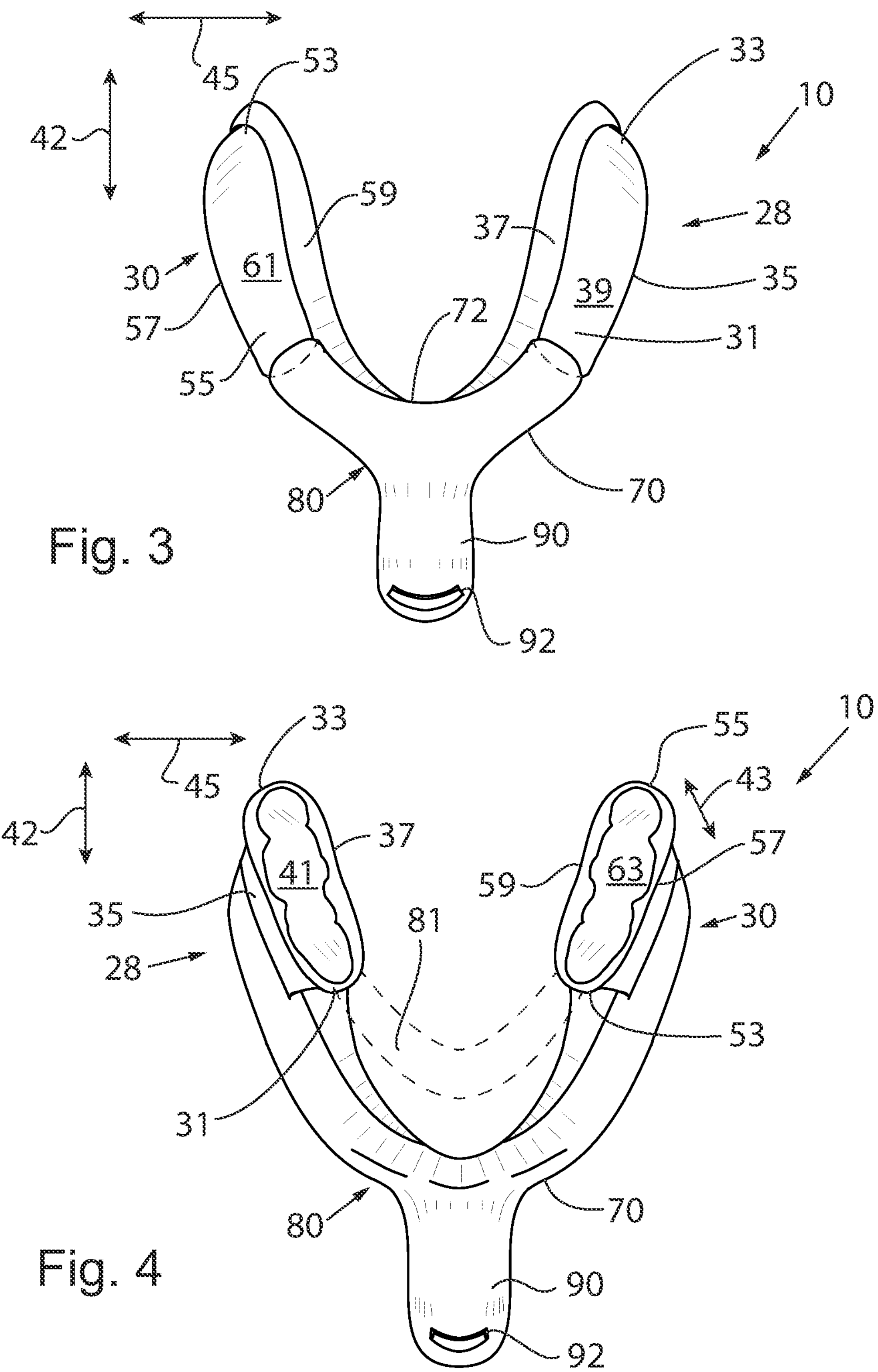
FIG. 3 is a top elevation view of the bite block of FIG. 1 showing an upper bridge joining the bilateral jaw spacers at an upper end of the bite block and positionable behind the patient's upper incisors.
FIG. 4 is a bottom perspective view of the bite block of FIG. 3 showing a gap between the bilateral jaw spacers at a lower end of the bite block.

Referring now to FIGS. 2 through 4, the bite block 10 comprises a left lateral jaw spacer 28 and a right lateral jaw spacer 30 positioned between the upper and lower posterior teeth of the left side and right side of the patient's jaw, respectively, and permanently joined by a bridge 80 that extends behind the patient's upper incisors (and optionally, lower incisors).

As seen in FIGS. 3 and 4, and a mirrored image of FIG. 2, the left lateral jaw spacer 28 is a triangular wedge block with a front end 31 opposite a rear end 33, joined on left and right ends by an outer lateral surface 35 opposite an inner lateral surface 37, and further joined on top and bottom ends by a top surface 39 contacting the teeth of the upper jaw 16 and a lower surface 41 contacting the teeth of the lower jaw 18.

The front end 31 of the left lateral jaw spacer 28 has a height that is greater than a height of the rear end 33 of the left lateral jaw spacer 28 to produce a wide front end tapering to a narrow rear thin edge. The narrow rear thin edge assists with the wedging of the left lateral jaw spacer 28 between the patient's upper and lower posterior teeth, for example, when the patient 14 is unconscious and the space between the patient's upper and lower posterior teeth is narrow. The front end 31 and the rear end 33 are rounded and smooth to prevent irritation with the buccal mucosa and the mouth cavity if there is contact.

The outer lateral surface 35 and the inner lateral surface 37 are generally opposed triangular surfaces extending along the buccal mucosa and the mouth cavity, respectively. The outer lateral surface 35 and the inner lateral surface 37 are generally rounded and smooth to prevent irritation if there is any contact with the buccal mucosa and the mouth cavity, however, the outer lateral surface 35 and the inner lateral surface 37 may be slightly concave to prevent rubbing contact.

The top surface 39 is a forwardly upwardly angled rectangular surface extending along the upper jaw 16 and the lower surface 41 is a generally forwardly downwardly angled rectangular surface extending along the lower jaw 18. The top surface 39 and lower surface 41 may be roughened to assist with gripping the teeth of the upper jaw 16 and teeth of the lower jaw 18 to prevent unwanted movement of the left lateral jaw spacer 28. In certain embodiments, as seen in FIG. 4, the top surface 39 and/or lower surface 41 may be molded to have indents that conform to the general shape of the crown of the posterior teeth of the upper jaw 16 and/or lower jaw 18, respectively. Desirable, the top surface 39 and/or lower surface 41 do not contact the buccal surfaces of the posterior teeth of the upper jaw 16 and lower jaw 18, respectively, to allow lateral access of the posterior teeth for brushing.

The left lateral jaw spacer 28 is configured to have a length 42 (extending between a front to rear of the jaw) that extends a length of a left maxillary first molar 32, second molar 34, and optionally, third molar (not shown) of the upper jaw 16, and the length of the left mandibular first molar 38, second molar 40, and optionally, third molar (not shown) of the lower jaw 18. The left maxillary first molar 32, second molar 34, and optionally, third molar (not shown) of the upper jaw 16 contact the top surface 39 of the left lateral jaw spacer 28 and the left mandibular first molar 38, second molar 40, and optionally, third molar (not shown) contact the lower surface 41 of the left lateral jaw spacer 28. In some embodiments, the left lateral jaw spacer 28 may not extend rearwardly of the second molar 34 or third molar (not shown) to prevent contact with the buccal surfaces at the back of the mouth.

Optionally, the left lateral jaw spacer 28 may extend forwardly to extend a length of a left maxillary first premolar 44 and second premolar 46 of the upper jaw 16 and the length of a left mandibular first premolar 48 and second premolar 50 of the lower jaw 18. The left maxillary first premolar 44 and second premolar 46 of the upper jaw 16 contact the top surface 39 of the left lateral jaw spacer 28 and the left mandibular first premolar 48 and second premolar 50 of the lower jaw 18 contact the lower surface 41 of the left lateral jaw spacer 28. In one embodiment, the left lateral jaw spacer 28 may have a width 45 (extending between a left side to a right side of the jaw) of about 4 to 10 mm and at least 4 mm, a length 42 (extending between a front to rear of the jaw) of about 40 to 60 mm and at least 40 mm, and a height 43 (extending between the upper jaw to lower jaw) of about 10 to 15 mm and at least 10 mm.

As seen in FIG. 2 through 4, in a similar construction, the right lateral jaw spacer 30 is a triangular wedge block with a front end 53 opposite a rear end 55, joined on left and right ends by an outer lateral surface 57 opposite an inner lateral surface 59, and further joined on top and bottom ends by a top surface 61 contacting the upper jaw 16 and a lower surface 63 contacting the lower jaw 18.

The front end 53 of the right lateral jaw spacer 30 has a height that is greater than a height of the rear end 55 of the right lateral jaw spacer 30 to produce a wide front end tapering to a narrow rear thin edge. The narrow rear thin edge assists with the wedging of the right lateral jaw spacer 30 between patient's upper and lower posterior teeth, for example, when the patient 14 is unconscious and the space between the patient's upper and lower posterior teeth is narrow. The front end 53 and the rear end 55 are rounded and smooth to prevent irritation with the buccal mucosa and the mouth cavity if there is contact.

The outer lateral surface 57 and the inner lateral surface 59 are generally opposed triangular surfaces extending along the buccal mucosa and the mouth cavity, respectively. The outer lateral surface 57 and the inner lateral surface 59 are generally rounded and smooth to prevent irritation if there is any contact with the buccal mucosa and the mouth cavity, however, the outer lateral surface 57 and the inner lateral surface 59 may be slightly concave to prevent rubbing contact.

The top surface 61 is a generally forwardly upwardly angled rectangular surface extending along the upper jaw 16 and the lower surface 63 is a generally forwardly downwardly angled rectangular surface extending along the lower jaw 18, respectively. The top surface 61 and lower surface 63 may be roughened to assist with gripping the teeth of the upper jaw 16 and lower jaw 18 to prevent movement of the right lateral jaw spacer 30. In certain embodiments, as seen in FIG. 4, the top surface 61 and/or lower surface 63 may be molded to have indents that conform to the general shape of the crown of the posterior teeth of the upper jaw 16 and/or lower jaw 18, respectively. Desirable, the top surface 61 and/or lower surface 63 do not contact the buccal surfaces of the posterior teeth of the upper jaw 16 and lower jaw 18, respectively to allow lateral access of the posterior teeth for brushing.

The right lateral jaw spacer 30 is configured to have a length 42 (extending between a front to rear of the jaw) that extends a length of the right maxillary first molar 32, second molar 34, and optionally, third molar (not shown) of the upper jaw 16, and the length of the right mandibular first molar 38, second molar 40, and optionally, third molar (not shown) of the lower jaw 18. The right maxillary first molar 32, second molar 34, and optionally, third molar (not shown) of the upper jaw 16 contact the top surface 61 of the right lateral jaw spacer 30 and the right mandibular first molar 38, second molar 40, and optionally, third molar (not shown) contact the lower surface 63 of the right lateral jaw spacer 30. In some embodiments, the right lateral jaw spacer 30 may not extend rearwardly of the second molar 34 or third molar (not shown) to prevent contact with the buccal surfaces at the back of the mouth.

Optionally, the right lateral jaw spacer 30 may extend forwardly to further extend a length of a right maxillary first premolar 44 and second premolar 46 of the upper jaw 16 and the length of a right mandibular first premolar 48 and second premolar 50 of the lower jaw 18. The right maxillary first premolar 44 and second premolar 46 of the upper jaw 16 contact the top surface 61 of the right lateral jaw spacer 30 and the right mandibular first premolar 48 and second premolar 50 of the lower jaw 18 contact the lower surface 63 of the right lateral jaw spacer 30.

In one embodiment, the right lateral jaw spacer 30 may have a width 45 (extending between a left side to a right side of the jaw) of about 4 to 10 mm and at least 4 mm, a length 42 (extending between a front to rear of the jaw) of about 40 to 60 mm and at least 40 mm, and a height 43 (extending between the upper jaw to lower jaw) of about 10 to 15 mm and at least 10 mm.

As referred to herein, the "posterior teeth" are teeth posterior to the patient's canine teeth 88 and may include any or all of the first premolar 44, 48, second premolar 46, 50, first molar 32, 38, second molar 34, 40, and third molar (not shown) of the patient. In this respect, it is understood that the left lateral jaw spacer 28 and right lateral jaw spacer 30 may extend along any or all of the first premolar 44, 48, second premolar 46, 50 first molar 32, 38, second molar 34, 40, and third molar (not shown) of the patient.

The upper bridge 80 joins the left lateral jaw spacer 28 and the right lateral jaw spacer 30 at a front of the bite block 10. The bridge 80 generally conforms to the forward curve of the upper jaw 16 to join the left lateral jaw spacer 28 and the right lateral jaw spacer 30 at their top surfaces 39, 61. Specifically, the bridge 80 includes a curved bar extending upwardly from the top surface 39 of the left lateral jaw spacer 28 and the top surface 61 of the right lateral jaw spacer 30 and forwardly in a U-shape along an alveolar process 82 above the lingual surface of the left and right maxillary central incisors 84, lateral incisors 86, and canines 88 of the upper jaw 16. The bridge 80 does not contact the alveolar process 82 or lingual surface of the incisors of the upper jaw 16 to prevent irritation or force from being applied on the surface. In some embodiments, the bridge 80 may be straight instead of curved.

The bridge 80 is a thin strip (in depth between front and rear surfaces) with a front surface 70 extending along the alveolar process 82 and lingual surface of the incisors of the upper jaw 16 and a rear surface 72 extending along the mouth cavity. For adult patients using average adult or large adult sizes, the bridge 80 may have a width 45 (extending from a left side to a right side of the jaw) of about 50 to 80 mm and at least 50 mm, which is less than an average width of the upper jaw 16, and a height 43 (extending from the upper jaw to a lower jaw) of about 5 to 7 mm and at least 5 mm, which is less than an average height of the left and right maxillary central incisors 84. For child or pediatric patients using small child or average child sizes, the bridge 80 may have a width (extending from a left side to a right side of the jaw) of about 25 to 40 mm and at least 25 mm, which is less than an average width of the upper jaw 16, and a height 43 (extending from the upper jaw to a lower jaw) of about 2.5 to 3.5 mm and at least 2.5 mm, which is less than an average height of the left and right maxillary central incisors 84. The front surface 70 and the rear surface 72 of the bridge 80 is generally rounded and smooth to prevent irritation with the buccal mucosa and the mouth cavity.

Optionally, the lower surface 41 of the of the left lateral jaw spacer 28 and the lower surface 63 of the right lateral jaw spacer 30 are joined by a second lower bridge 81 (shown dotted in FIGS. 2 and 4) which is similar to the upper bridge 80 and includes a curved bar extending therebetween and curving forwardly in a U-shape along the alveolar process 82 below the lingual surface of the left and right mandibular central incisors 85, lateral incisors 87, and canines 88 of the lower jaw 18. However, in the preferred embodiment, the second bridge 81 is omitted to prevent dislocation of the bite block 10 when the patient 14 pushes upward on the lower second bridge 81 with their tongue.

The bridge 80 (or the second bridge 81) may support a support tab 90 extending outside of the patient's mouth and supporting the attachment of a fastener 94 anchoring the external end 24 of the endotracheal tube 20 to the support tab 90. The support tab 90 may be a curved, tongue shaped tab extending forwardly from the front surface 70 of the bridge 80, below the left and right maxillary central incisors 84, and forwardly in front of the left and right maxillary central incisors 84. The support tab 90 and fastener 94 extend outwardly from the patient's mouth and prevents the support tab 90, fastener 94, and endotracheal tube 20 from contacting or putting pressure on the patient's lips which may cause mouth sores and irritation to the lips. It is understood that the support tab 90 may support the endotracheal tube 20 in any manner, for example, from above or below the endotracheal tube 20, which effectively removes the endotracheal tube 20 from contacting the patient's lips.

In certain embodiments, the support tab 90 extends horizontally in a forward direction from the front surface 70 of the bridge 80 without any curvature of the support tab 90. However, in certain embodiments, the support tab 90 may curve downwardly in order to avoid the left and right maxillary central incisors 84, and then continue to extend forwardly at an upward angle in front of the left and right maxillary central incisors 84. The support tab 90 may extend approximately 15 to 30 mm and at least 15 mm forwardly from the front surface 70 of the bridge 80.

The support tab 90 may include a slot or hole 92 permitting the fastener 94 such as a cable tie, zip tie, strap, and the like to anchor the endotracheal tube 20 to the bite block 10. For example, the fastener 94 may be tied through the hole 92 of the support tab 90 and around the external end 24 of the endotracheal tube 20 in a secure manner which prevents the external end 24 of the endotracheal tube 20 from being separated from the bite block 10. The position of the support tab 90 at the upper end of the bite block 10 prevents the patient from displacing the bite block 10 and the endotracheal tube 20 with their tongue.

Referring again to FIG. 1, when inserted inside the mouth 12 of the patient 14, the bite block 10 holds the mouth 12 in an open mouth position, with the upper jaw 16 separated from the lower jaw 18 at an angle of mouth opening (0) with respect to the internal temporomandibular joint (TMJ), providing a bite block interincisal distance 100 between the incisal edge of the maxillary central incisors 84 of the upper jaw 16 and the incisal edge of the mandibular central incisors 85 of the lower jaw 18. In one embodiment, the angle of mouth opening (θ) may be at least 20 degrees and at least 25 degrees and at least 30 degrees to provide the bite block interincisal distance 100 described below.

The bite block interincisal distance 100 is a minimum distance required to prevent force (biting from the patient's teeth or jaw) from being applied on the endotracheal tube 20 which extends between the incisors 84, 86 and canines 88 of the upper jaw 16 and the incisors 85, 86 and canines 88 of the lower jaw 18. In this respect, the bite block interincisal distance 100 may be at least as wide as the outer diameter of the endotracheal tube 20, for example, the bite block interincisal distance 100 may be about 10 to 20 mm and at least 10 mm and at least 11 mm and at least 12 mm and at least 13 mm and at least 14 mm and at least 15 mm and at least 20 mm. A normal maximum range of interincisal distance is between 53 to 58 mm therefore the bite block interincisal distance 100 is much less than the maximum range of interincisal distance 100 for the average patient 14 and should not cause discomfort to the patient 14.

The bite block 10 may be manufactured of a singularly molded flexible material or elastomeric material such as rubber, synthetic rubber, or composite resin. The bite block 10 is absent any metal material so that the bite block 10 may be compatible with medical imaging without introducing interaction and interference, but still having the desired toughness and strength to endure biting forces up to 300 to 600 Newtons without damage.

It is understood that a kit of differently sized bite blocks 10 may be provided with different standardized sizes, for example, small child, average child, average adult, and large adult, in order to fit the different jaw sizes of a majority of patients. The standardized sizes may accommodate a range of jaw widths that exists between differently sized patients, for example, providing varying widths of the bridge 80. The standardized sizes may also accommodate the range of angles of mouth opening (θ) that exists between differently sized patients, for example, providing varying heights of the left lateral jaw spacer 28 and the right lateral jaw spacer 30 to provide different mouth opening angles (θ).

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112 (f) unless the words "means for" or "step for" are explicitly used in the particular claim.

What we claim is:

1. A bite block device for inhibiting a biting force on an endotracheal tube extending through a human patient's mouth, the bite block device comprising:

a first molar spacer configured to contact left maxillary posterior teeth on a top surface and left mandibular posterior teeth on a bottom surface;

a second molar spacer configured to contact right maxillary posterior teeth on a top surface and right mandibular posterior teeth on a bottom surface;

a bridge connecting a front portion of the first molar spacer at a first end to a front portion of the second molar spacer at a second end, the bridge being positioned fully behind a lingual surface of maxillary incisors; and a tab extending forwardly from the bridge to avoid maxillary incisors and out of the patient's mouth beyond lips of the patient for attachment to an endotracheal tube.

2. The bite block of claim 1 wherein the first molar spacer and second molar spacer are fixedly attached to the bridge.

3. The bite block of claim 1 wherein the first end and second end of the bridge extend upwardly from the top end of the first molar spacer and the top end of the second molar spacer, respectively.

4. The bite block of claim 3 wherein the tab dips downwardly as it extends forward to avoid the maxillary incisors and further extends at an upward angle as it extends forward beyond the maxillary incisors.

5. The bite block of claim 1 wherein the bridge does not contact the patient's buccal mucosa or lips.

6. The bite block of claim 1 wherein a distance between the first end and the second end of the bridge is approximately equal to a width of an upper jaw of the patient.

7. The bite block of claim 6 wherein the distance between the first end and the second end of the bridge is at least 25 mm.

8. The bite block of claim 1 further comprising a medical tubing attached to the tab.

9. The bite block of claim 1 wherein the first and second molar spacers are wedge shaped blocks tapering from a broad front end to a narrow rear end.

10. The bite block of claim 9 wherein a height of the broad front end of the first and second molar spacers is at least 10 mm.

11. The bite block of claim 1 wherein a length of the first and second molar spacers extending across the left and right maxillary posterior teeth of the patient is at least 40 mm.

12. The bite block of claim 1 wherein an angle of mouth opening with respect to a patient's temporomandibular joint is at least 20 degrees.

13. The bite block of claim 1 wherein the first and second molar spacer are configured to create an interincisal distance between an incisal edge of maxillary central incisors of an upper jaw of the patient and an incisal edge of mandibular central incisors of a lower jaw of the patient of at least 10 mm.

14. The bite block of claim 1 wherein the first and second molar spacer do not contact buccal surfaces of the posterior teeth of the patient.

15. The bite block of claim 1 further comprising a second bridge connecting the bottom end of the first molar spacer and the bottom end of the second molar spacer and extending forwardly to a front end configured to extend along a lingual surface of mandibular incisors.

16. A method of inhibiting a biting force on an endotracheal tube extending through a human patient's mouth, comprising:

providing a bite block having a first molar spacer configured to contact left maxillary posterior teeth on a top surface and left mandibular posterior teeth on a bottom surface;

a second molar spacer configured to contact right maxillary posterior teeth on a top surface and right mandibular posterior teeth on a bottom surface; and a bridge connecting a front portion of the first molar spacer at a first end to a front portion of the second molar spacer at a second end the bridge being positioned fully behind a lingual surface of maxillary incisors;

a tab extending forwardly from the bridge to avoid maxillary incisors and out of the patient's mouth beyond lips of the patient for attachment to an endotracheal tube; and positioning the first molar spacer between the left maxillary posterior teeth and the left mandibular posterior teeth;

positioning the second molar spacer between the right maxillary posterior teeth and right mandibular posterior teeth; and positioning the bridge along the lingual surface of the maxillary incisors.

17. The method of claim 16 further comprising distributing a biting force of the patient onto the first molar spacer and the second molar spacer.

18. The method of claim 16 further comprising attaching an endotracheal tube to the tab outside of the patient's mouth.

* * * * *